United States Patent
Awasthi et al.

(10) Patent No.: US 11,873,361 B2
(45) Date of Patent: Jan. 16, 2024

(54) OPHTHALMIC DEVICES

(71) Applicant: Bausch + Lomb Ireland Limited, Dublin (IE)

(72) Inventors: Alok Kumar Awasthi, Pittsford, NY (US); Kristen Rae Hovinga, Honeoye Falls, NY (US); Emily Abrams Gabriel, Pittsford, NY (US); Kevin Jacob DeRyke, Webster, NY (US); Jade J. Russell, Perry, NY (US); James Anthony DiBella, Jr., Macedon, NY (US); Alana Ingham, Hilton, NY (US)

(73) Assignee: BAUSCH + LOMB IRELAND LIMITED, Dublin (IE)

(*) Notice: Subject to any disclaimer, the term of this patent is extended or adjusted under 35 U.S.C. 154(b) by 0 days.

(21) Appl. No.: 17/836,282

(22) Filed: Jun. 9, 2022

(65) Prior Publication Data
US 2023/0089707 A1    Mar. 23, 2023

Related U.S. Application Data

(60) Provisional application No. 63/239,343, filed on Aug. 31, 2021.

(51) Int. Cl.
| | |
|---|---|
| *C08F 283/06* | (2006.01) |
| *A61L 27/16* | (2006.01) |
| *A61L 27/50* | (2006.01) |
| *C08F 226/10* | (2006.01) |
| *C08F 283/12* | (2006.01) |
| *C08K 5/18* | (2006.01) |

(Continued)

(52) U.S. Cl.
CPC ............ *C08F 283/06* (2013.01); *A61L 27/16* (2013.01); *A61L 27/50* (2013.01); *C08F 226/10* (2013.01); *C08F 283/12* (2013.01); *C08K 5/18* (2013.01); *C08K 5/42* (2013.01); *A61L 2430/16* (2013.01); *G02B 1/043* (2013.01)

(58) Field of Classification Search
CPC ..................................................... G02B 1/043
See application file for complete search history.

(56) References Cited

U.S. PATENT DOCUMENTS

| | | |
|---|---|---|
| 3,408,429 A | 10/1968 | Wichterle |
| 3,660,545 A | 5/1972 | Wichterle |
| 4,113,224 A | 9/1978 | Clark et al. |

(Continued)

FOREIGN PATENT DOCUMENTS

| | | |
|---|---|---|
| KR | 1020200037002 A | 4/2020 |
| WO | 2020176444 A1 | 3/2020 |

(Continued)

*Primary Examiner* — Michael F Pepitone
(74) *Attorney, Agent, or Firm* — Ryan, Mason & Lewis, LLP

(57) ABSTRACT

An ophthalmic device for slowing, inhibiting or preventing myopia progression which is a polymerization product of a monomeric mixture comprising (a) greater than 50 wt. %, based on the total weight of the monomeric mixture, of one or more non-silicone-containing hydrophilic monomers; (b) one or more crosslinking agents; and (c) one or more red-light blocking compounds blocking greater than 5% to about 25% of red-light transmission through the ophthalmic device at a wavelength of from about 550 nm to about 800 nm, wherein the one or more red-light blocking compounds have one or more ethylenically unsaturated reactive end groups.

20 Claims, 5 Drawing Sheets

(51) Int. Cl.
C08K 5/42 (2006.01)
G02B 1/04 (2006.01)

(56) References Cited

U.S. PATENT DOCUMENTS

| | | |
|---|---|---|
| 4,197,266 A | 4/1980 | Clark et al. |
| 4,555,732 A | 11/1985 | Tuhro |
| 4,910,277 A | 3/1990 | Bambury et al. |
| 5,070,215 A | 12/1991 | Bambury et al. |
| 5,271,875 A | 12/1993 | Appleton et al. |
| 5,944,853 A | 8/1999 | Molock et al. |
| 7,915,323 B2 | 3/2011 | Awasthi et al. |
| 7,994,356 B2 | 8/2011 | Awasthi et al. |
| 8,420,711 B2 | 4/2013 | Awasthi |
| 8,703,891 B2 | 4/2014 | Broad |
| 8,827,447 B2 | 9/2014 | Awasthi et al. |
| 8,865,929 B2 | 10/2014 | Xu et al. |
| 8,937,110 B2 | 1/2015 | Alli et al. |
| 8,937,111 B2 | 1/2015 | Alli et al. |
| 9,039,174 B2 | 5/2015 | Awasthi et al. |
| 9,156,934 B2 | 10/2015 | Alli et al. |
| 9,244,197 B2 | 1/2016 | Alli et al. |
| 9,429,684 B2 | 8/2016 | Wang et al. |
| 2014/0200287 A1 | 7/2014 | Xu et al. |
| 2019/0212583 A1 | 7/2019 | Wu |

FOREIGN PATENT DOCUMENTS

| | | |
|---|---|---|
| WO | 2021086269 A1 | 5/2021 |
| WO | PCT/EP2022/066569 | 1/2023 |

OPHTHALMIC DEVICES

PRIORITY CLAIM

The present application claims priority to U.S. Provisional Patent Application Ser. No. 63/239,343, entitled "Ophthalmic Devices," filed Aug. 31, 2021, the content of which is incorporated by reference herein in its entirety.

BACKGROUND

This disclosure generally relates to ophthalmic devices such as contact lenses for slowing, inhibiting or preventing myopia progression.

Ophthalmic devices such as contact lenses are made of various polymeric materials, including rigid gas permeable materials, soft elastomeric materials, and soft hydrogel materials. The majority of contact lenses sold today are made of soft hydrogel materials. Hydrogels are a cross-linked polymeric system that absorb and retain water, typically 10 to 80 percent by weight. Hydrogel lenses are commonly prepared by polymerizing a lens-forming monomeric mixture. In the case of silicone hydrogel lenses, a silicone-containing monomer is copolymerized with a hydrophilic monomer.

In the field of ophthalmic devices, various physical and chemical properties such as, for example, oxygen permeability, wettability, material strength and stability are but a few of the factors that must be carefully balanced in order to provide a useable contact lens. For example, since the cornea receives its oxygen supply from contact with the atmosphere, oxygen permeability is an important characteristic for certain contact lens material. Wettability also is important in that, if the lens is not sufficiently wettable, it does not remain lubricated and therefore cannot be worn comfortably in the eye. Accordingly, the optimum contact lens would have at least both excellent oxygen permeability and excellent tear fluid wettability.

SUMMARY

In accordance with an illustrative embodiment, an ophthalmic device for slowing, inhibiting or preventing myopia progression which is a polymerization product of a monomeric mixture comprising (a) greater than 50 wt. %, based on the total weight of the monomeric mixture, of one or more non-silicone-containing hydrophilic monomers; (b) one or more crosslinking agents; and (c) one or more red-light blocking compounds blocking greater than about 5% to about 25% of red-light transmission through the ophthalmic device at a wavelength of from about 550 nanometers (nm) to about 800 nm, wherein the one or more red-light blocking compounds have one or more ethylenically unsaturated reactive end groups.

In accordance with another illustrative embodiment, a method for making an ophthalmic device for slowing, inhibiting or preventing myopia progression which comprises (a) providing a monomeric mixture comprising (i) greater than 50 wt. %, based on the total weight of the monomeric mixture, of one or more non-silicone-containing hydrophilic monomers; (ii) one or more crosslinking agents; and (iii) one or more red-light blocking compounds blocking greater than about 5% to about 25% of red-light transmission through the ophthalmic device at a wavelength of from about 550 nm to about 800 nm, wherein the one or more red-light blocking compounds have one or more ethylenically unsaturated reactive end groups; (b) subjecting the monomeric mixture to polymerizing conditions to provide a polymerized device; and (c) hydrating the polymerized device.

In accordance with yet another illustrative embodiment, a method for slowing, inhibiting or preventing myopia progression in a subject in need thereof comprises (a) providing an ophthalmic device which is a polymerization product of a monomeric mixture comprising (i) greater than 50 wt. %, based on the total weight of the monomeric mixture, of one or more non-silicone-containing hydrophilic monomers; (ii) one or more crosslinking agents; and (iii) one or more red-light blocking compounds blocking greater than about 5% to about 25% of red-light transmission through the ophthalmic device at a wavelength of from about 550 nm to about 800 nm, wherein the one or more red-light blocking compounds have one or more ethylenically unsaturated reactive end groups; and (b) inserting the ophthalmic device into an eye of the subject.

BRIEF DESCRIPTION OF THE DRAWINGS

Exemplary embodiments of the present disclosure will be described below in more detail, with reference to the accompanying drawings, of which.

DETAILED DESCRIPTION

Figure 1:
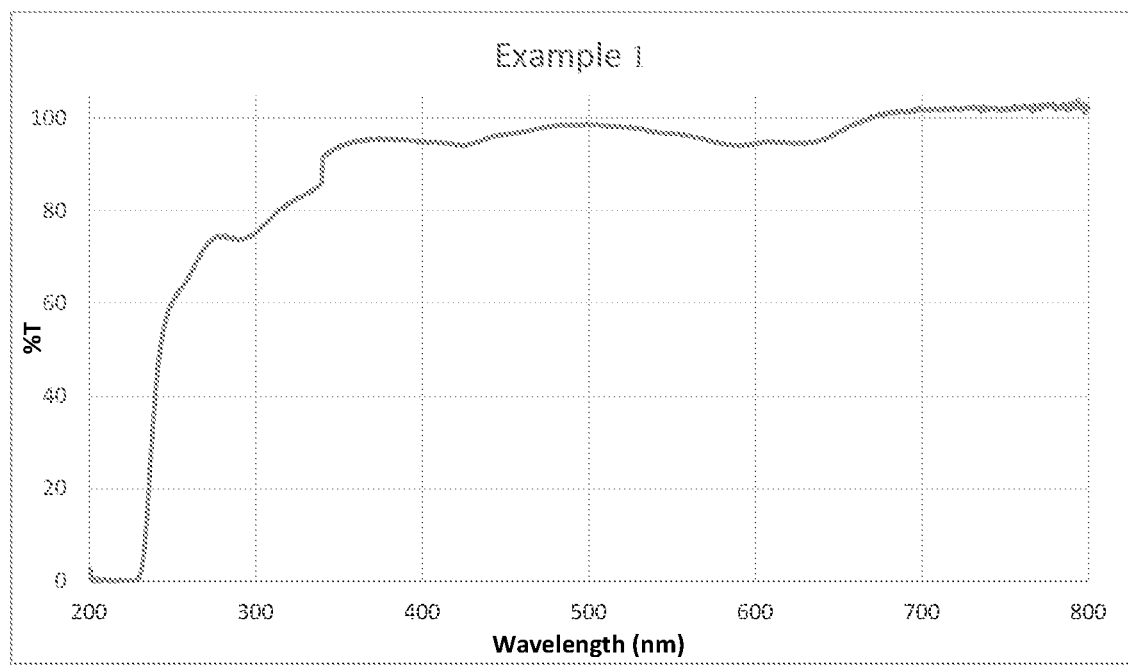
FIG. 1 is a graph illustrating the percent transmission of red-light through the lens of Example 1.

Various illustrative embodiments described herein are directed to ophthalmic devices derived from one or more red-light blocking compounds for slowing, inhibiting or preventing myopia progression in a subject in need thereof, e.g., a human. In general, natural light consists of different monochromatic lights with different wavelengths, which may not focus on the same plane on the retina. A longer wavelength monochromatic light can focus on the plane behind the retina whereas a shorter wavelength monochromatic light can focus on the plane in front of the retina. The different focuses of the lights may contribute to a backward displacement of the retina toward the eye's image plane leading to elongation of the eye. This can result in various pathologies including myopia.

Myopia ("nearsightedness") is a vision condition where objects near to a viewer appear clear, but objects that are spaced farther away from the viewer get progressively blurred. Myopia can be caused by multiple reasons. One factor in many cases of myopia is an elongated axial length of the eye. Myopia occurs when the focal point of the focused light is formed before the retina. In other words, the focal point of the light rays entering the eye stop short of the retina. Thus, myopic eyes focus in front of the retinal plane. Myopia typically develops because the axial length of the eye grows to be longer than the focal length of the optical components of the eye, that is, the eye grows too long.

It is believed that excessive stimulation of L cones in a person's eye (especially in children), may result in non-optimal eye lengthening and myopia. By spectrally filtering red-light using an ophthalmic device containing one or more red-light blocking compounds, myopia can be further reduced in a wearer. However, present dyes (or colorants) of such red-light blocking compounds typically used to manufacture tinted soft contact lenses often leach out and the lenses lose their original tint when subjected to sterilization conditions or during prolonged storage. Thus, there is a need for an improved ophthalmic device which can filter and/or block red-light thereby inhibiting or preventing myopia in a wearer of the ophthalmic device.

Accordingly, the ophthalmic devices described herein overcome the foregoing problems and advantageously provide for at least one of slowing, inhibiting or preventing myopia progression by blocking greater than about 5% and up to about 25% of red-light transmission through the ophthalmic device at a wavelength of from about 550 nanometers (nm) to about 800 nm. In non-limiting illustrative embodiments, the ophthalmic devices described herein advantageously slow, inhibit or prevent myopia progression in a subject by adding one or more red-light blocking compounds blocking greater than 5% to about 25% of red-light transmission through the ophthalmic device at a wavelength of from about 550 nm to about 800 nm, wherein the one or more red-light blocking compounds have one or more ethylenically unsaturated reactive end groups to a monomeric mixture comprising (a) greater than 50 wt. %, based on the total weight of the monomeric mixture, of one or more non-silicone-containing hydrophilic monomers; and (b) one or more crosslinking agents; and polymerizing the monomeric mixture to form an ophthalmic device.

The ophthalmic devices disclosed herein are intended for direct contact with body tissue or body fluid. As used herein, the term "ophthalmic device" refers to devices that reside in or on the eye. These devices can provide optical correction, wound care, drug delivery, diagnostic functionality or cosmetic enhancement or effect or a combination of these properties. Useful ophthalmic devices include, but are not limited to, ophthalmic lenses such as soft contact lenses, e.g., a soft, hydrogel lens, soft, non-hydrogel lens and the like, hard contact lenses, e.g., a hard, gas permeable lens material and the like, intraocular lenses, overlay lenses, ocular inserts, optical inserts and the like. As is understood by one skilled in the art, a lens is considered to be "soft" if it can be folded back upon itself without breaking.

In illustrative non-limiting embodiments, an ophthalmic device described herein is a polymerization product of a monomeric mixture comprising: (a) greater than 50 wt. %, based on the total weight of the monomeric mixture, of one or more non-silicone-containing hydrophilic monomers; (b) one or more crosslinking agents, and (c) one or more red-light blocking compounds blocking greater than 5% to about 25% of red-light transmission through the ophthalmic device at a wavelength of from about 550 nm to about 800 nm, wherein the one or more red-light blocking compounds have one or more ethylenically unsaturated reactive end groups.

In an illustrative embodiment, the monomeric mixture comprises greater than 50 wt. % and up to 90 wt. %, based on the total weight of the monomeric mixture, of one or more non-silicone-containing hydrophilic monomers. In an illustrative embodiment, the monomeric mixture comprises greater than 50 wt. % and up to 85 wt. %, based on the total weight of the monomeric mixture, of one or more non-silicone-containing hydrophilic monomers. In an illustrative embodiment, the monomeric mixture comprises greater than 50 wt. % and up to 80 wt. %, based on the total weight of the monomeric mixture, of one or more non-silicone-containing hydrophilic monomers.

As used herein, the term "(meth)" denotes an optional methyl substituent. Thus, for example, terms such as "(meth)acrylate" denotes either methacrylate or acrylate, and "(meth)acrylamide" denotes either methacrylamide or acrylamide.

Suitable non-silicone-containing hydrophilic monomers include, for example, unsaturated carboxylic acids, acrylamides, vinyl lactams, poly(alkyleneoxy)(meth)acrylates, hydroxyl-containing-(meth)acrylates, hydrophilic vinyl carbonates, hydrophilic vinyl carbamates, hydrophilic oxazolones, and poly(alkene glycols) functionalized with polymerizable groups and the like and mixtures thereof. Representative examples of unsaturated carboxylic acids include methacrylic acid, acrylic acid and the like and mixtures thereof. Representative examples of amides include alkylamides such as N,N-dimethylacrylamide, N,N-dimethylmethacrylamide and the like and mixtures thereof. Representative examples of cyclic lactams include N-vinyl-2-pyrrolidone, N-vinyl caprolactam, N-vinyl-2-piperidone and the like and mixtures thereof. Representative examples of hydroxyl-containing (meth)acrylates include 2-hydroxyethyl methacrylate, glycerol methacrylate and the like and mixtures thereof. Representative examples of functionalized poly(alkene glycols) include poly(diethylene glycols) of varying chain length containing monomethacrylate or dimethacrylate end caps. In one embodiment, the poly(alkene glycol) polymer contains at least two alkene glycol monomeric units. Still further examples are the hydrophilic vinyl carbonate or vinyl carbamate monomers disclosed in U.S. Pat. No. 5,070,215, and the hydrophilic oxazolone monomers disclosed in U.S. Pat. No. 4,910,277. Other suitable hydrophilic monomers will be apparent to one skilled in the art. Mixtures of the foregoing non-silicone-containing hydrophilic monomers can also be used in the monomeric mixtures herein.

In one illustrative embodiment, a monomeric mixture will include one or more non-silicone-containing hydrophilic monomers which are one or more cyclic lactams. In another illustrative embodiment, a monomeric mixture will include one or more non-silicone-containing hydrophilic monomers which are N-vinyl caprolactam.

The monomeric mixture further includes one or more crosslinking agents. Suitable crosslinking agents for use herein are known in the art. A useful crosslinking agent can have at least two polymerizable functional groups. For example, in an illustrative non-limiting embodiment, suitable one or more cross-linking agents include one or more crosslinking agents containing at least two ethylenically unsaturated reactive end groups, wherein the ethylenically unsaturated reactive end groups are (meth)acrylate-containing reactive end groups, one or more crosslinking agents containing at least two ethylenically unsaturated reactive end groups wherein at least one of the ethylenically unsaturated reactive end groups is a non-(meth)acrylate reactive end group and mixtures thereof.

In an illustrative embodiment, useful one or more crosslinking agents containing at least two ethylenically unsaturated reactive end groups, wherein the ethylenically unsaturated reactive end groups are (meth)acrylate-containing reactive end groups include one or more di-, tri- or tetra (meth)acrylate-containing crosslinking agents.

In an illustrative embodiment, useful one or more di-, tri- or tetra(meth)acrylate-containing crosslinking agents include alkanepolyol di-, tri- or tetra(meth)acrylate-containing crosslinking agents such as, for example, one or more alkylene glycol di(meth)acrylate crosslinking agents, one or more alkylene glycol tri(meth)acrylate crosslinking agents, one or more alkylene glycol tetra(meth)acrylate crosslinking agents, one or more alkanediol di(meth)acrylate crosslinking agents, alkanediol tri(meth)acrylate crosslinking agents, alkanediol tetra(meth)acrylate crosslinking agents, agents, one or more alkanetriol di(meth)acrylate crosslinking agents, alkanetriol tri(meth)acrylate crosslinking agents, alkanetriol tetra(meth)acrylate crosslinking agents, agents, one or more alkanetetraol di(meth)acrylate crosslinking agents, alkanetetraol tri(meth)acrylate crosslinking agents, alkanetetraol tetra(meth)acrylate crosslinking agents and the like and mixtures thereof.

In an illustrative embodiment, one or more alkylene glycol di(meth)acrylate crosslinking agents include tetraethylene glycol dimethacrylate, ethylene glycol di(meth)acrylates having up to about 10 ethylene glycol repeating units, butyleneglycol di(meth)acrylate and the like. In one embodiment, one or more alkanediol di(meth)acrylate crosslinking agents include butanediol di(meth)acrylate crosslinking agents, hexanediol di(meth)acrylate and the like. In one embodiment, one or more alkanetriol tri(meth)acrylate crosslinking agents are trimethylol propane trimethacrylate crosslinking agents. In one embodiment, one or more alkanetetraol tetra(meth)acrylate crosslinking agents are pentaerythritol tetramethacrylate crosslinking agents.

In an illustrative embodiment, useful one or more crosslinking agents containing at least two ethylenically unsaturated reactive end groups wherein at least one of the ethylenically unsaturated reactive end groups is a non-(meth)acrylate reactive end group include one or more di-, tri- or tetracarbamate-containing crosslinking agents, one or more di-, tri- or tetracarbonate-containing crosslinking agents, one or more isocyanurate-containing crosslinking agents and the like and mixtures thereof.

Representative examples of one or more di-, tri- or tetracarbamate-containing crosslinking agents include one or more di(N-vinylcarbamate)-containing crosslinking agents, one or more di(N-allylcarbamate)-containing crosslinking agents, one or more di(O-vinylcarbamate)-containing crosslinking agents, one or more di(O-allylcarbamate)-containing crosslinking agents, one or more tri(N-vinylcarbamate)-containing crosslinking agents, one or more tri(N-allylcarbamate)-containing crosslinking agents, one or more tri(O-vinylcarbamate)-containing crosslinking agents, one or more tri(O-allylcarbamate)-containing crosslinking agents, one or more tetra(N-vinylcarbamate)-containing crosslinking agents, one or more tetra (N-allylcarbamate)-containing crosslinking agents, one or more tetra (O-vinylcarbamate)-containing crosslinking agents, one or more tetra(O-allylcarbamate)-containing crosslinking agents, and the like and mixtures thereof.

Representative examples of one or more di-, tri- or tetracarbonate-containing crosslinking agents include a di(O-vinylcarbonate)-containing crosslinking agent, a di(O-allylcarbonate)-containing crosslinking agent, a tri(O-vinylcarbonate)-containing crosslinking agent, a tri(O-allylcarbonate)-containing crosslinking agent, a tetra(O-vinylcarbonate)-containing crosslinking agent, a tetra(O-allylcarbonate)-containing crosslinking agent, and the like and mixtures thereof.

Representative examples of one or more isocyanurate-containing crosslinking agents include one or more diallyl isocyanurate, triallyl isocyanurate, divinyl isocyanurate, trivinyl isocyanurate, and the like and mixtures thereof.

In an embodiment, one or more di-carbamate-containing crosslinking agents include bis (N-vinyl carbamates) having the following structure:

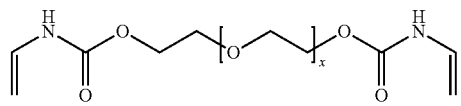

wherein x is from 0 to 10.

In an embodiment, one or more di-carbamate-containing crosslinking agents include bis (O-vinyl carbamates) having the following structure:

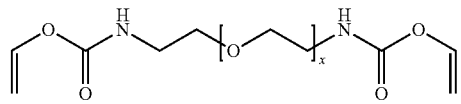

wherein x is from 0 to 10.

In an embodiment, one or more di-carbamate-containing crosslinking agents include diethylene glycol bis(N-vinylcarbamate), diethylene glycol bis(O-allylcarbamate), and the like and mixtures thereof.

In an embodiment, the one or more second crosslinking agents are selected from the group consisting of diethylene glycol bis(N-vinylcarbamate), diethylene glycol bis(N-allylcarbamate), diethylene glycol bis(O-vinylcarbamate), diethylene glycol bis(O-allylcarbamate), and mixtures thereof, 1,4-butanediol bis(N-vinylcarbamate), ethylene glycol bis(O-vinyl carbonate), diethylene glycol bis(O-vinyl carbonate), 1,4-butanediol bis(O-vinyl carbonate) and mixtures thereof.

In an embodiment, the one or more crosslinking agents containing at least two ethylenically unsaturated reactive end groups include at least one allyl-containing reactive end group and at least one (meth)acrylate-containing reactive end group. In one embodiment, the one or more second crosslinking agents include allyl methacrylate.

In an embodiment, suitable crosslinking agents include divinylbenzene, allyl methacrylate, ethyleneglycol dimethacrylate, tetraethyleneglycol dimethacrylate, polyethyleneglycol dimethacrylate, vinyl carbonate derivatives of the glycol dimethacrylates, and methacryloxyethyl vinylcarbonate.

In general, the one or more crosslinking agents are present in the monomeric mixture in an ophthalmic device-forming amount. In an embodiment, the one or more crosslinking agents are present in the monomeric mixture in an amount of about 0.1 to about 2.0 wt. %, based on the total weight of the monomeric mixture.

The monomeric mixture further includes one or more red-light blocking compounds blocking greater than about 5% to about 25% of red-light transmission through the ophthalmic device at a wavelength of from about 550 nm to about 800 nm, wherein the one or more red-light blocking compounds have one or more ethylenically unsaturated reactive end groups. In an illustrative embodiment, the one or more red-light blocking compounds comprise one or more red-light blocking compounds blocking greater than about 5% to about 25% of red-light transmission through the ophthalmic device at a wavelength of from about 550 nm to about 700 nm, wherein the one or more red-light blocking compounds have one or more ethylenically unsaturated reactive end groups. In an illustrative embodiment, the one or more red-light blocking compounds comprise one or more red-light blocking compounds blocking greater than about 5% to about 25% of red-light transmission through the ophthalmic device at a wavelength of from about 650 nm to about 680 nm, wherein the one or more red-light blocking compounds have one or more ethylenically unsaturated reactive end groups.

In another illustrative embodiment, the one or more red-light blocking compounds comprise one or more red-light blocking compounds blocking from about 10% to about 15% of red-light transmission through the ophthalmic device at a wavelength of from about 550 nm to about 800 nm, wherein the one or more red-light blocking compounds have one or more ethylenically unsaturated reactive end groups. In an illustrative embodiment, the one or more red-light blocking compounds comprise one or more red-light blocking compounds blocking from about 10% to about 15% of red-light transmission through the ophthalmic device at a wavelength of from about 550 nm to about 700 nm, wherein the one or more red-light blocking compounds have one or more ethylenically unsaturated reactive end groups. In an illustrative embodiment, the one or more red-light blocking compounds comprise one or more red-light blocking compounds blocking greater from about 10% to about 15% of red-light transmission through the ophthalmic device at a wavelength of from about 650 nm to about 680 nm, wherein the one or more red-light blocking compounds have one or more ethylenically unsaturated reactive end groups.

In an illustrative embodiment, the one or more red-light blocking compounds comprise one or more red-light blocking compounds blocking from greater than 5% to about 25% of red-light transmission through the ophthalmic device at a wavelength of from about 550 nm to about 800 nm, wherein the one or more red-light blocking compounds have one or more methacrylate-containing reactive end groups. In one illustrative embodiment, the one or more red-light blocking compounds comprise one or more red-light blocking compounds blocking greater than 5% to about 25% of red-light transmission through the ophthalmic device at a wavelength of from about 550 nm to about 700 nm, wherein the one or more red-light blocking compounds have one or more methacrylate-containing reactive end groups. In an illustrative embodiment, the one or more red-light blocking compounds comprise one or more red-light blocking compounds blocking greater than 5% to about 25% of red-light transmission through the ophthalmic device at a wavelength of from about 650 nm to about 680 nm, wherein the one or more red-light blocking compounds have one or more methacrylate-containing reactive end groups.

In an illustrative embodiment, the one or more red-light blocking compounds comprise one or more red-light blocking compounds blocking from about 10% to about 15% of red-light transmission through the ophthalmic device at a wavelength of from about 550 nm to about 800 nm, wherein the one or more red-light blocking compounds have one or more methacrylate-containing reactive end groups. In an illustrative embodiment, the one or more red-light blocking compounds comprise one or more red-light blocking compounds blocking from about 10% to about 15% of red-light transmission through the ophthalmic device at a wavelength of from about 550 nm to about 700 nm, wherein the one or more red-light blocking compounds have one or more methacrylate-containing reactive end groups. In an illustrative embodiment, the one or more red-light blocking compounds comprise one or more red-light blocking compounds blocking greater from about 10% to about 15% of red-light transmission through the ophthalmic device at a wavelength of from about 650 nm to about 680 nm, wherein the one or more red-light blocking compounds have one or more methacrylate-containing reactive end groups.

In an illustrative embodiment, ethylenically unsaturated reactive end groups include by way of example, (meth)acrylate end groups, vinyl end groups, acrylamide end groups and the like. In one embodiment, an ethylenically unsaturated reactive end group is a methacrylate-containing reactive end group. Suitable methacrylate-containing reactive end groups can be those represented by the structure:

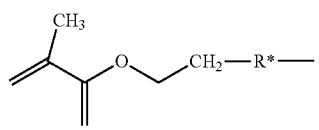

wherein R* is a linking group or bond. Suitable linking groups include, for example, any divalent hydrocarbon radical or moiety such as independently straight or branched, substituted or unsubstituted $C_1$-$C_{30}$ alkyl group, a substituted or unsubstituted $C_3$-$C_{30}$ cycloalkyl group, a substituted or unsubstituted $C_4$-$C_{30}$ cycloalkylalkyl group, a substituted or unsubstituted $C_3$-$C_{30}$ cycloalkenyl group, a substituted or unsubstituted $C_6$-$C_{30}$ aryl group, a substituted or unsubstituted $C_7$-$C_{30}$ arylalkyl group and substituted and unsubstituted ether-containing groups. The divalent hydrocarbon radical or moiety of the linking group can optionally contain a heteroatom such as sulfur, e.g., a sulfone, in the chain.

Representative examples of alkyl groups for use herein include, by way of example, a straight or branched alkyl chain radical containing carbon and hydrogen atoms of from 1 to about 30 carbon atoms or from 1 to about 12 carbon atoms or from 1 to about 6 carbon atoms with or without unsaturation, to the rest of the molecule, e.g., methyl, ethyl, n-propyl, 1-methylethyl (isopropyl), n-butyl, n-pentyl, methylene, ethylene, etc., and the like to form heteroalkyl groups.

Representative examples of cycloalkyl groups for use herein include, by way of example, a substituted or unsubstituted non-aromatic mono or multicyclic ring system of about 3 to about 30 carbon atoms or from 3 to about 6 carbon atoms such as, for example, cyclopropyl, cyclobutyl, cyclopentyl, cyclohexyl, perhydronapththyl, adamantyl and norbornyl groups, bridged cyclic groups or sprirobicyclic groups, e.g., spiro-(4,4)-non-2-yl and the like, optionally containing one or more heteroatoms, e.g., O and N, and the like to form heterocycloalkyl groups.

Representative examples of cycloalkylalkyl groups for use herein include, by way of example, a substituted or unsubstituted cyclic ring-containing radical containing from about 4 to about 30 carbon atoms or from 3 to about 6 carbon atoms directly attached to the alkyl group which are then attached to the main structure of the monomer at any carbon from the alkyl group that results in the creation of a stable structure such as, for example, cyclopropylmethyl, cyclobutylethyl, cyclopentylethyl and the like, wherein the cyclic ring can optionally contain one or more heteroatoms, e.g., O and N, and the like to form heterocycloalkylalkyl groups.

Representative examples of cycloalkenyl groups for use herein include, by way of example, a substituted or unsubstituted cyclic ring-containing radical containing from about 3 to about 30 carbon atoms or from 3 to about 6 carbon atoms with at least one carbon-carbon double bond such as, for example, cyclopropenyl, cyclobutenyl, cyclopentenyl and the like, wherein the cyclic ring can optionally contain one or more heteroatoms, e.g., O and N, and the like to form heterocycloalkenyl groups.

Representative examples of aryl groups for use herein include, by way of example, a substituted or unsubstituted monoaromatic or polyaromatic radical containing from about 6 to about 30 carbon atoms such as, for example, phenyl, naphthyl, tetrahydronapthyl, indenyl, biphenyl and the like, optionally containing one or more heteroatoms, e.g., O and N, and the like to form heteroaryl groups.

Representative examples of arylalkyl groups for use herein include, by way of example, a substituted or unsubstituted aryl group as defined herein directly bonded to an alkyl group as defined herein, e.g., —CH$_2$C$_6$H$_5$, —C$_2$H$_4$C$_6$H$_5$ and the like, wherein the aryl group can optionally contain one or more heteroatoms, e.g., O and N, and the like to form heteroarylalkyl groups.

Representative examples of ether or polyether containing groups for use herein include, by way of example, an alkyl ether, cycloalkyl ether, cycloalkylalkyl ether, cycloalkenyl ether, aryl ether, arylalkyl ether wherein the alkyl, cycloalkyl, cycloalkylalkyl, cycloalkenyl, aryl, and arylalkyl groups are as defined herein. Exemplary ether or polyether-containing groups include, by way of example, alkylene oxides, poly(alkylene oxide)s such as ethylene oxide, propylene oxide, butylene oxide, poly(ethylene oxide)s, poly(ethylene glycol)s, poly(propylene oxide)s, poly(butylene oxide)s and mixtures or copolymers thereof, an ether or polyether group of the general formula —(R$^{14}$OR$^{15}$)$_t$, wherein R$^{14}$ is a bond, a substituted or unsubstituted alkyl, cycloalkyl or aryl group as defined herein and R$^{15}$ is a substituted or unsubstituted alkyl, cycloalkyl or aryl group as defined herein and t is at least 1, and the like.

In one illustrative embodiment, a class of one or more red-light blocking compounds can be represented by those compounds having a structure of Formula (I):

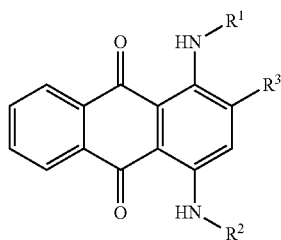

(I)

wherein R$^1$ and R$^2$ are hydrogen or an ethylenically unsaturated reactive end group, with at least one of R$^1$ and R$^2$ being an ethylenically unsaturated reactive end group; and R$^3$ is hydrogen or a sulfonate group.

In one illustrative embodiment, another class of one or more red-light blocking compounds can be represented by those compounds having a structure of Formula (II):

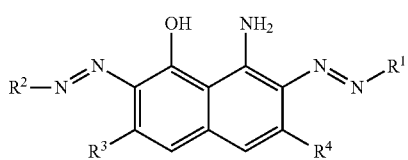

(II)

wherein R$^1$ and R$^2$ are hydrogen or an ethylenically unsaturated reactive end group, with at least one of R$^1$ and R$^2$ being an ethylenically unsaturated reactive end group; and R$^3$ and R$^4$ are independently hydrogen or a sulfonate group.

The one or more red-light blocking compounds can be obtained by methods known in the art or are commercially available from such sources as Pharnorcia Inc. and Sigma Aldrich.

In an illustrative embodiment, the one or more red-light blocking compounds can be present in the monomeric mixture in an amount ranging from about 0.005 wt. % to about 0.30 wt. %, based on the total weight of the monomeric mixture. In another illustrative embodiment, the one or more red-light blocking compounds can be present in the monomeric mixture in an amount ranging from about 0.02 wt. % to about 0.30 wt. %, based on the total weight of the monomeric mixture. In another illustrative embodiment, the one or more red-light blocking compounds can be present in the monomeric mixture in an amount ranging from about 0.05 wt. % to about 0.30 wt. %, based on the total weight of the monomeric mixture. In another illustrative embodiment, the one or more red-light blocking compounds can be present in the monomeric mixture in an amount ranging from about 0.05 wt. % to about 0.20 wt. %, based on the total weight of the monomeric mixture.

The monomeric mixture may further include one or more non-bulky organosilicon-containing monomers. An "organosilicon-containing monomer" as used herein contains at least one [siloxanyl] or at least one [silyl-alkyl-siloxanyl] repeating unit, in a monomer, macromer or prepolymer. In one embodiment, one or more non-bulky organosilicon-containing monomers can comprise a compound represented by a structure of Formula (III):

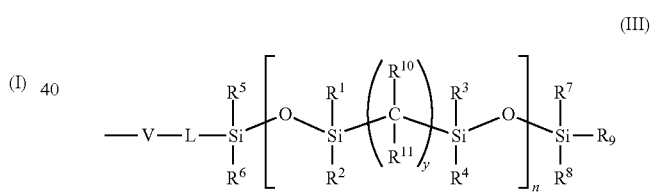

(III)

wherein V is ethylenically unsaturated polymerizable group, L is a linker group or a bond; R$^1$, R$^2$, R$^3$, R$^4$, R$^5$, R$^6$, R$^7$, R$^8$, and R$^9$ are independently H, C$_1$ to C$_{12}$ alkyl, halo alkyl, C$_3$ to C$_{12}$ cycloalkyl, heterocycloalkyl, C$_2$ to C$_{12}$ alkenyl, haloalkenyl, or C$_6$ to C$_{12}$ aromatic; R$^{10}$, and R$^{11}$ are independently H or C$_1$ to C$_{12}$ alkyl wherein at least one of R$^{10}$ and R$^{11}$ is hydrogen; y is 2 to 7 and n is 1 to 100 or from 1 to 20.

Ethylenically unsaturated polymerizable groups are well known to those skilled in the art. Suitable ethylenically unsaturated polymerizable groups include, for example, (meth)acrylates, vinyl carbonates, O-vinyl carbamates, N-vinyl carbamates, and (meth)acrylamides.

Linker groups can be any divalent radical or moiety and include, for example, substituted or unsubstituted C$_1$ to C$_{12}$ alkyl, alkyl ether, alkenyls, alkenyl ethers, halo alkyls, substituted or unsubstituted siloxanes, and monomers capable of propagating ring opening.

In one embodiment, V is a (meth)acrylate, L is a C$_1$ to C$_{12}$ alkylene, R$^1$, R$^2$, R$^3$, R$^4$, R$^5$, R$^6$, R$^7$, R$^8$, and R$^9$ are independently a C$_1$ to C$_{12}$ alkyl, R$^{10}$ and R$^{11}$ are independently H, y is 2 to 7 and n is 3 to 8.

In one embodiment, V is a (meth)acrylate, L is a $C_1$ to $C_6$ alkyl, $R^1$, $R^2$, $R^3$, $R^4$, $R^5$, $R^6$, $R^7$, $R^8$, and $R^9$ are independently a $C_1$ to $C_6$ alkyl, $R^{10}$ and $R^{11}$ are independently H, y is 2 to 7 and n is 1 to 20.

Non-bulky organosilicon-containing monomers represented by a structure of Formula III are known in the art, see, e.g., U.S. Pat. Nos. 7,915,323, 7,994,356, 8,420,711, 8,827, 447 and 9,039,174, the contents of which are incorporated by reference herein.

In one embodiment, one or more non-bulky organosilicon-containing monomers can comprise a compound represented by a structure of Formula IV:

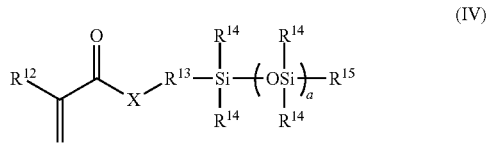

(IV)

wherein $R^{12}$ is H or methyl; X is O or $NR^{16}$; wherein $R^{16}$ is selected from H, or $C_1$ to $C_4$ alkyl, which may be further substituted with one or more hydroxyl groups, and in some embodiments is H or methyl; $R^{13}$ is a divalent alkyl group, which may further be functionalized with a group selected from the group consisting of ether groups, hydroxyl groups, carbamate groups and combinations thereof, and in another embodiment $C_1$ to $C_6$ alkylene groups which may be substituted with ether, hydroxyl and combinations thereof, and in yet another embodiment $C_1$ or $C_3$ to $C_4$ alkylene groups which may be substituted with ether, hydroxyl and combinations thereof; each $R^{14}$ is independently a phenyl or $C_1$ to $C_4$ alkyl which may be substituted with fluorine, hydroxyl or ether, and in another embodiment each $R^{14}$ is independently selected from ethyl and methyl groups, and in yet another embodiment, each $R^{14}$ is methyl; $R^{15}$ is a $C_1$ to $C_4$ alkyl; a is 2 to 50, and in some embodiments 5 to 15.

Non-bulky organosilicon-containing monomers represented by a structure of Formula IV are known in the art, see, e.g., U.S. Pat. Nos. 8,703,891, 8,937,110, 8,937,111, 9,156, 934 and 9,244,197, the contents of which are incorporated by reference herein.

In an illustrative embodiment, the one or more non-bulky organosilicon-containing monomers can be present in the monomeric mixture in an amount ranging from about 5 wt. % to about 50 wt. %, based on the total weight of the monomeric mixture. In one embodiment, the one or more non-bulky organosilicon-containing monomers can be present in the monomeric mixture in an amount ranging from about 15 wt. % to about 45 wt. %, based on the total weight of the monomeric mixture.

The monomeric mixture may further include one or more bulky siloxane monomers. Representative examples of applicable siloxane monomers include bulky polysiloxanylalkyl(meth)acrylic monomers. In a suitable embodiment, a suitable bulky siloxane monomer is represented by the structure of Formula V:

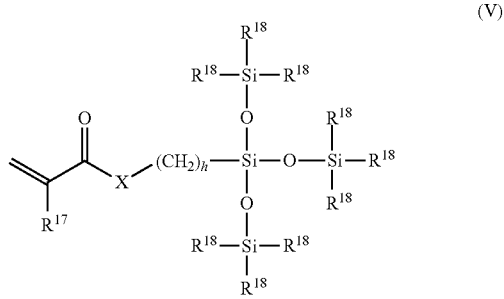

(V)

wherein X denotes —O— or —$NR^{19}$—; wherein $R^{19}$ is hydrogen or a $C_1$-$C_4$ alkyl; each $R^{17}$ independently denotes hydrogen or methyl; each $R^{18}$ independently denotes a lower alkyl radical such as a $C_1$-$C_6$ alkyl, a phenyl radical or a group represented by:

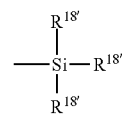

wherein each $R^{18'}$ independently denotes a lower alkyl such as a $C_1$-$C_6$ alkyl, or a phenyl radical; and his 1 to 10.

In one embodiment, a suitable bulky siloxane monomer is a bulky polysiloxanylalkyl carbamate monomer as generally depicted in Formula VI:

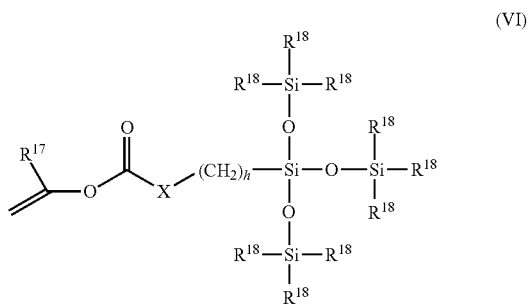

(VI)

wherein X denotes —N $R^{19}$—, wherein $R^{19}$ denotes hydrogen or a $C_1$-$C_4$ alkyl; $R^{17}$ denotes hydrogen or methyl; each $R^{18}$ independently denotes a lower alkyl radical such as a $C_1$-$C_6$ alkyl radical, a phenyl radical or a group represented by:

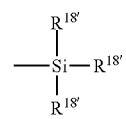

wherein each $R^{18'}$ independently denotes a lower alkyl radical such as a $C_1$-$C_6$ alkyl radical, or a phenyl radical; and h is 1 to 10.

Suitable one or more bulky siloxane monomers include, for example, methacryloxypropyl tris(trimethyl siloxy)silane ("TRIS"), pentamethyl di siloxanyl methylmethacrylate, tris(trimethyl siloxy)methacryloxy propyl silane, phenyltretramethyl-disloxanylethyl acrylate, methyldi (trimethylsiloxy)methacryloxymethyl silane, 3-[tris(trimethyl siloxy)silyl]propyl vinyl carbamate (TRIS-VC), 3-[tris(trimethyl siloxy)silyl]propyol allyl carbamate, 3-[tris(trimethyl siloxy)silyl]propyl vinyl carbonate and mixtures thereof.

In an illustrative embodiment, the one or more bulky siloxane monomers can be present in the monomeric mixture in an amount ranging from about 5 wt. % to about 50 wt. %, based on the total weight of the monomeric mixture. In one embodiment, the one or more bulky siloxane monomers can be present in the monomeric mixture in an amount ranging from about 15 wt. % to about 45 wt. %, based on the total weight of the monomeric mixture.

The monomeric mixture may further include one or more hydrophobic monomers. Suitable hydrophobic monomers include ethylenically unsaturated hydrophobic monomers such as, for example, (meth)acrylates-containing hydrophobic monomers, N-alkyl (meth)acrylamides-containing hydrophobic monomers, alkyl vinylcarbonates-containing hydrophobic monomers, alkyl vinylcarbamates-containing hydrophobic monomers, fluoroalkyl (meth)acrylates-containing hydrophobic monomers, N-fluoroalkyl (meth)acrylamides-containing hydrophobic monomers, N-fluoroalkyl vinylcarbonates-containing hydrophobic monomers, N-fluoroalkyl vinylcarbamates-containing hydrophobic monomers, silicone-containing (meth)acrylates-containing hydrophobic monomers, (meth)acrylamides-containing hydrophobic monomers, vinyl carbonates-containing hydrophobic monomers, vinyl carbamates-containing hydrophobic monomers, styrenic-containing hydrophobic monomers, polyoxypropylene (meth)acrylate-containing hydrophobic monomers and the like and mixtures thereof.

In one illustrative embodiment, wherein the one or more hydrophobic monomers is represented by the structure of Formula VII:

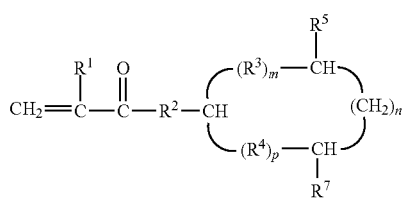

(VII)

wherein $R^1$ is methyl or hydrogen; $R^2$ is —O— or —NH—; $R^3$ and $R^4$ are independently a divalent radical selected from the group consisting of —$CH_2$—, —CHOH— and —$CHR^6$—; $R^5$ and $R^6$ are independently a branched $C_3$-$C_8$ alkyl group; $R^7$ is hydrogen or —OH; n is an integer of at least 1, and m and p are independently 0 or an integer of at least 1, provided that the sum of m, p and n is 2, 3, 4 or 5.

Representative examples of one or more hydrophobic monomers represented by the structure of Formula VII include, but are not limited to, 4-t-butyl-2-hydroxycyclohexyl methacrylate (TBE); 4-t-butyl-2-hydroxycyclopentyl methacrylate; 4-t-butyl-2-hydroxycyclohexyl methacrylamide (TBA); 6-isopentyl-3-hydroxycyclohexyl methacrylate; 2-isohexyl-5-hydroxycyclopentyl methacrylamide, 4-t-butylcyclohexyl methacrylate, isobornyl methacrylate, adamntyl methacrylate, n-butyl methacrylate, n-hexyl methacrylate, lauryl methacrylate, benzyl methacrylate, and the like. In one embodiment, one or more hydrophobic monomers (b) include compounds of Formula VII wherein $R^3$ is —$CH_2$—, m is 1 or 2, p is 0, and the sum of m and n is 3 or 4.

In an illustrative embodiment, the one or more hydrophobic monomers will be present in the monomeric mixture in an amount ranging from about 0.5 to about 25 wt. %, based on the total weight of the monomeric mixture. In one embodiment, the one or more hydrophobic monomers will be present in the monomeric mixture in an amount ranging from about 1 to about 10 wt. %, based on the total weight of the monomeric mixture.

The monomeric mixture may further contain, as necessary and within limits not to impair the purpose and effect of the present disclosure, various additives such as an antioxidant, wetting agents, toughening agents and the like and other constituents as is well known in the art.

In an embodiment, a suitable wetting agent can be, for example, glycerin, propylene glycol, mono or disaccharide, polyethylene glycol, ethoxylated glucose, and combinations thereof. In one embodiment, a suitable wetting agent can be, for example, a polymer containing carboxylic acid functionality, such as a polymer containing polyacrylic acid (PAA). Specific coating wetting agents include P(vinylpyrrolidinone(VP)-co-acrylic acid (AA)), P(methylvinylether-alt-maleic acid), P(acrylic acid-graft-ethyleneoxide), P(acrylic acid-co-methacrylic acid), P(acrylamide-co-AA), P(acrylamide-co-AA), P(AA-co-maleic), P(butadiene-maleic acid) and P(N-vinylpyrrolidone-co-vinyl acetate), and polyvinylalcohol.

The ophthalmic devices of the illustrative embodiments described herein, e.g., contact lenses or intraocular lenses, can be prepared by polymerizing the foregoing monomeric mixtures to form a product that can be subsequently formed into the appropriate shape by, for example, lathing, injection molding, compression molding, cutting and the like. For example, in producing contact lenses, the initial mixture may be polymerized in tubes to provide rod-shaped articles, which are then cut into buttons. The buttons may then be lathed into contact lenses.

Alternately, the ophthalmic devices such as contact lenses may be cast directly in molds, e.g., polypropylene molds, from the mixtures, e.g., by spincasting and static casting methods. Spincasting methods are disclosed in U.S. Pat. Nos. 3,408,429 and 3,660,545, and static casting methods are disclosed in U.S. Pat. Nos. 4,113,224, 4,197,266, and 5,271,875. Spincasting methods involve charging the mixtures to be polymerized to a mold, and spinning the mold in a controlled manner while exposing the mixture to a radiation source such as UV light. Static casting methods involve charging the monomeric mixture between two mold sections, one mold section shaped to form the anterior lens surface and the other mold section shaped to form the posterior lens surface, and curing the mixture while retained in the mold assembly to form a lens, for example, by free radical polymerization of the mixture. Examples of free radical reaction techniques to cure the lens material include thermal radiation, infrared radiation, electron beam radiation, gamma radiation, ultraviolet (UV) radiation, and the like; or combinations of such techniques may be used. U.S. Pat. No. 5,271,875 describes a static cast molding method that permits molding of a finished lens in a mold cavity defined by a posterior mold and an anterior mold. As an additional method, U.S. Pat. No. 4,555,732 discloses a process where an excess of a monomeric mixture is cured by spincasting in a mold to form a shaped article having an anterior lens surface and a relatively large thickness, and the posterior surface of the cured spincast article is subsequently lathed to provide a contact lens having the desired thickness and posterior lens surface.

Polymerization may be facilitated by exposing the mixture to heat and/or radiation, such as ultraviolet light, visible light, or high energy radiation. A polymerization initiator may be included in the mixture to facilitate the polymerization step. Representative examples of free radical thermal polymerization initiators include organic peroxides such as acetyl peroxide, lauroyl peroxide, decanoyl peroxide, stearoyl peroxide, benzoyl peroxide, tertiarylbutyl peroxypivalate, peroxydicarbonate, and the like. Representative UV initiators are those known in the art and include benzoin methyl ether, benzoin ethyl ether, Darocure® 1173, 1164, 2273, 1116, 2959, 3331 (EM Industries) and Irgacure® 651 and 184 (Ciba-Geigy), 2,2'Azobis(2-methylpropionitrile) (VAZO 64) and the like. Generally, the initiator will be employed in the monomeric mixture at a concentration of about 0.01 to about 5 percent by weight of the total mixture.

Polymerization is generally performed in a reaction medium, such as, for example, a solution or dispersion using a solvent, e.g., water or an alkanol containing from 1 to 4 carbon atoms such as methanol, ethanol or propan-2-ol. Alternatively, a mixture of any of the above solvents may be used.

Generally, polymerization can be carried out for about 15 minutes to about 72 hours, and under an inert atmosphere of, for example, nitrogen or argon. If desired, the resulting polymerization product can be dried under vacuum, e.g., for about 5 to about 72 hours or left in an aqueous solution prior to use.

Polymerization of the mixtures will yield a polymer, that when hydrated, preferably forms a hydrogel. When producing a hydrogel lens, the mixture may further include at least a diluent that is ultimately replaced with water when the polymerization product is hydrated to form a hydrogel. Generally, the water content of the hydrogel is as described hereinabove, i.e., at least about 45 weight percent, or at least about 50 weight percent. The amount of diluent used should be less than about 50 weight percent and in most cases, the diluent content will be less than about 30 weight percent. However, in a particular polymer system, the actual limit will be dictated by the solubility of the various monomers in the diluent. In order to produce an optically clear copolymer, it is important that a phase separation leading to visual opacity does not occur between the comonomers and the diluent, or the diluent and the final copolymer.

Furthermore, the maximum amount of diluent which may be used will depend on the amount of swelling the diluent causes the final polymers. Excessive swelling will or may cause the copolymer to collapse when the diluent is replaced with water upon hydration. Suitable diluents include, but are not limited to, ethylene glycol; glycerine; liquid poly(ethylene glycol); alcohols; alcohol/water mixtures; ethylene oxide/propylene oxide block copolymers; low molecular weight linear poly(2-hydroxyethyl methacrylate); glycol esters of lactic acid; formamides; ketones; dialkylsulfoxides; butyl carbitol; boric acid esters of polyhydric alcohols such as boric acid esters of glycerol and the like and mixtures thereof.

If necessary, it may be desirable to remove residual diluent from the lens before edge-finishing operations which can be accomplished by evaporation at or near ambient pressure or under vacuum. An elevated temperature can be employed to shorten the time necessary to evaporate the diluent. The time, temperature and pressure conditions for the solvent removal step will vary depending on such factors as the volatility of the diluent and the specific monomeric components, as can be readily determined by one skilled in the art. If desired, the mixture used to produce the hydrogel lens may further include crosslinking and wetting agents known in the prior art for making hydrogel materials.

In the case of intraocular lenses, the monomeric mixtures to be polymerized may further include a monomer for increasing the refractive index of the resultant polymerized product. Examples of such monomers include aromatic (meth) acrylates, such as phenyl (meth)acrylate, 2-phenylethyl (meth)acrylate, 2-phenoxyethyl methacrylate, and benzyl (meth)acrylate.

The ophthalmic devices such as contact lenses obtained herein may be subjected to optional machining operations. For example, the optional machining steps may include buffing or polishing a lens edge and/or surface. Generally, such machining processes may be performed before or after the product is released from a mold part, e.g., the lens is dry released from the mold by employing vacuum tweezers to lift the lens from the mold, after which the lens is transferred by means of mechanical tweezers to a second set of vacuum tweezers and placed against a rotating surface to smooth the surface or edges. The lens may then be turned over in order to machine the other side of the lens.

The lens may then be transferred to individual lens packages containing a buffered saline solution. The saline solution may be added to the package either before or after transfer of the lens. Appropriate packaging designs and materials are known in the art. A plastic package is releasably sealed with a film. Suitable sealing films are known in the art and include foils, polymer films and mixtures thereof. The sealed packages containing the lenses are then sterilized to ensure a sterile product. Suitable sterilization means and conditions are known in the art and include, for example, autoclaving.

As one skilled in the art will readily appreciate other steps may be included in the molding and packaging process described above. Such other steps can include, for example, coating the formed lens, surface treating the lens during formation (e.g., via mold transfer), inspecting the lens, discarding defective lenses, cleaning the mold halves, reusing the mold halves, and the like and combinations thereof.

The following examples are provided to enable one skilled in the art to practice the invention and are merely illustrative. The examples should not be read as limiting the scope of the invention as defined in the claims.

In the examples, the following abbreviations are used.

DMA: N,N-dimethylacrylamide.

HEMA: 2-hydroxyethyl methacrylate.

NVP: N-vinyl-2-pyrrolidone.

EGDMA: Ethylene glycol dimethacrylate.

SIGMA: (3-methacryloxy-2-hydroxypropoxy)propyl bis (trimethylsiloxy)methylsilane TRIS: 3-[Tris(trimethylsiloxy)silyl]propyl methacrylate.

Vazo™ 64: azo bis-isobutylnitrile (AIBN).

Irgacure 819: a photoinitiator for free radical polymerization available from Sigma Aldrich.

Poloxamer: Pluronic 407 dimethacrylate having the following structure:

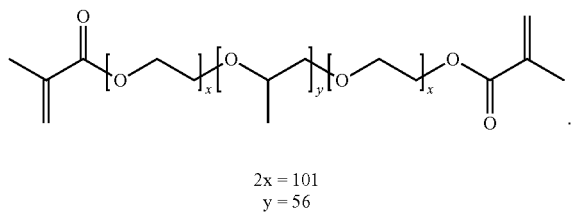

2x = 101
y = 56

CIX-4: a compound having the structure:

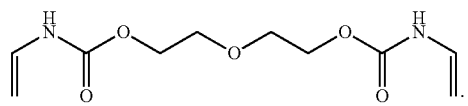 [SMILES: C=CNC(=O)OCCOCCOC(=O)NC=C]

MPEG silane 16: a compound having the following structure and available from Momentive:

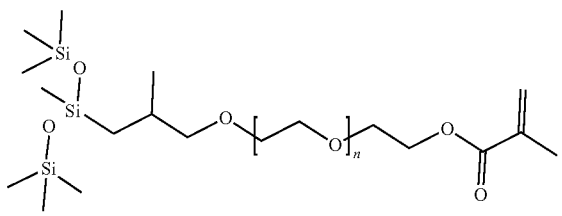

m-peg silane n=16

Ma2D37: a compound having the following structure and available from Shin-Etsu and Gelest:

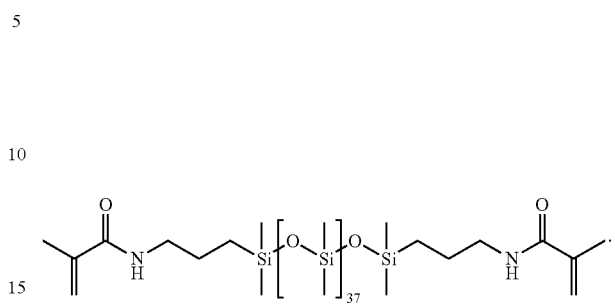

M1EDS6: a compound having the following structure and available from Gelest:

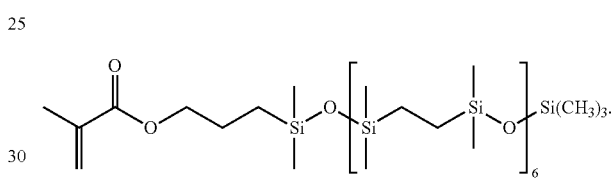

Methacrylated Reactive Black 5: a compound having the following structure was prepared by the reaction of Reactive Black 5 and HEMA: Reactive Black 5 was purchased from Sigma Aldrich, HEMA was purchased from Evonik.

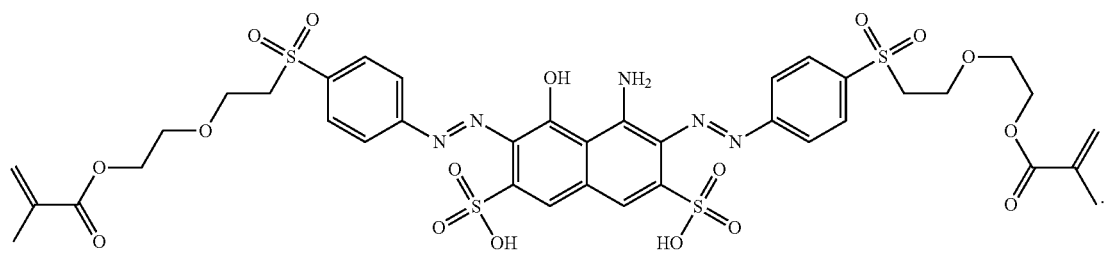 [SMILES: C=C(C)C(=O)OCCOCCS(=O)(=O)c1ccc(/N=N/c2c(S(=O)(=O)O)cc3cc(S(=O)(=O)O)c(/N=N/c4ccc(S(=O)(=O)CCOCCOC(=O)C(=C)C)cc4)c(O)c3c2N)cc1]

Methacrylated Reactive Blue 19: a compound having the following structure was prepared by the reaction of Reactive Blue 19 and HEMA: Reactive Blue 19 was purchased from Sigma Aldrich, HEMA was purchased from Evonik

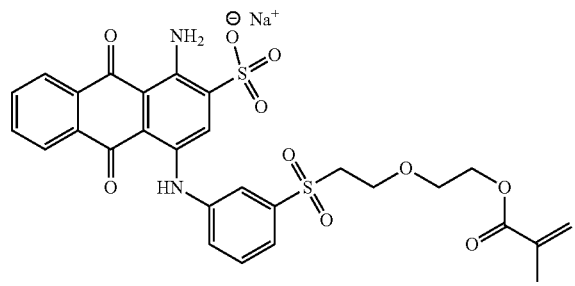 [SMILES: [Na+] ; C=C(C)C(=O)OCCOCCS(=O)(=O)c1cccc(Nc2cc(S(=O)(=O)[O-])c(N)c3c2C(=O)c2ccccc2C3=O)c1]

Reactive Blue 247: a compound having the following structure and available from Pharnocia:

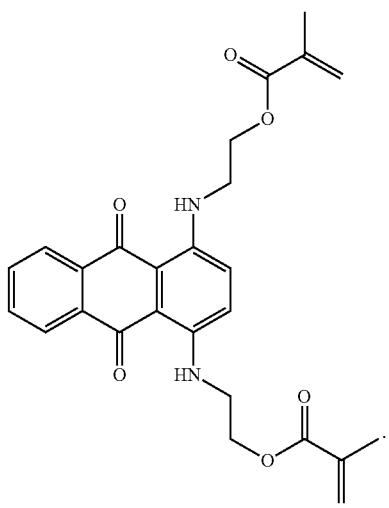 [SMILES: C=C(C)C(=O)OCCNc1ccc(NCCOC(=O)C(=C)C)c2c1C(=O)c1ccccc1C2=O]

Examples 1 and 2

A monomeric mix was made by mixing the following components, listed in Table 1 at amounts per weight.

TABLE 1

| Formulation | Ex. 1 | Ex. 2 |
| --- | --- | --- |
| NVP | 75.60 | 52.81 |
| HEMA | 1.92 | 6.02 |
| EGDMA | 0.11 | 0.50 |
| AMA | 0.42 | — |
| Poloxamer407 DM | 4.20 | — |
| TBE | 8.43 | — |
| Propylene Glycol | 8.43 | 10.00 |
| Vazo 64 | 0.42 | 0.20 |
| MPEG-Silane16 | — | 8.52 |
| TRIS | — | 7.96 |
| SIGMA | — | 13.97 |
| Reactive Blue 19 | 0.05 | 0.20 |

The monomeric mixtures were cast into contact lenses by introducing the monomeric mixture to a polypropylene mold assembly. Then, the mold assembly and monomeric mixture were thermally cured for about 3.0 hours to form a contact lens. The resultant contact lenses were released from the mold assembly, extracted twice in 100% water for 10 minutes each and placed in a borated buffer solution (BBS) before being autoclaved.

Figure 2:
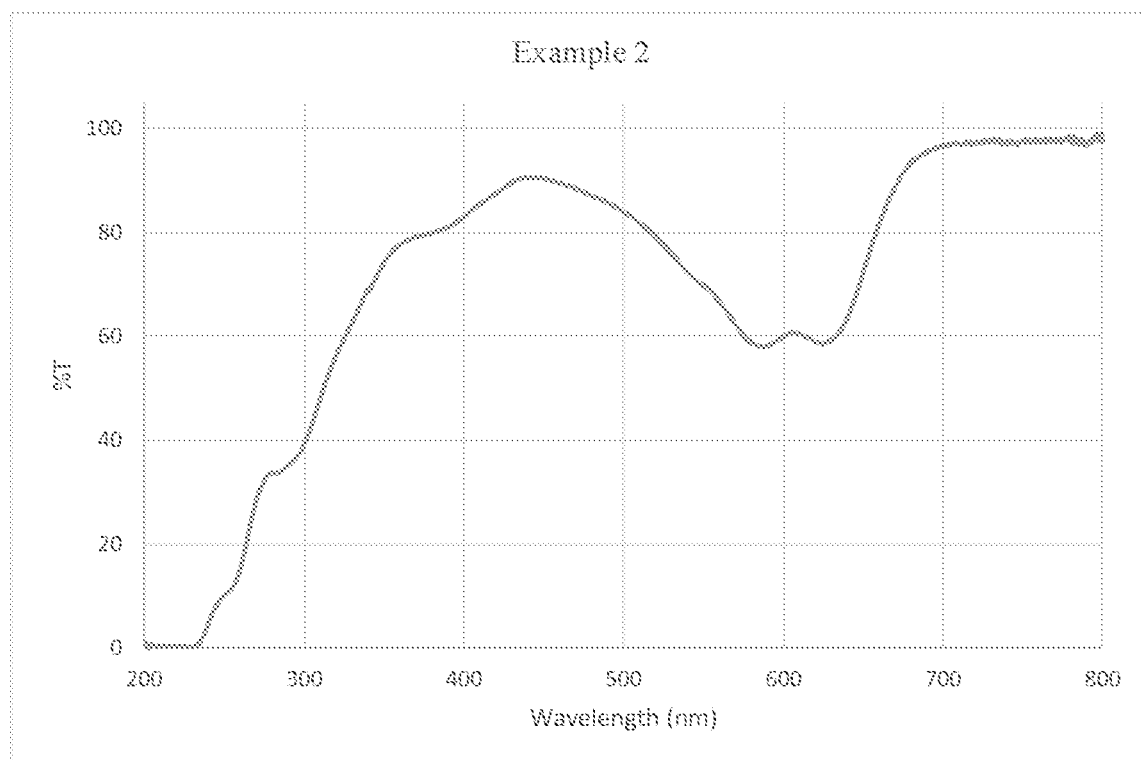
FIG. 2 is a graph illustrating the percent transmission of red-light through the lens of Example 2.

The lenses of Example 1 and 2 were then individually placed onto a horizontal integrating sphere for contact lens measurement. The transmittance spectrum was obtained from 200 nm to 800 nm. FIGS. 1 and 2 are each a graph illustrating the percent transmission of red-light through the lens of Examples 1 and 2, respectively.

Examples 3-5

A monomeric mix was made by mixing the following components, listed in Table 2 at amounts per weight.

TABLE 2

| Formulation | Ex. 3 | Ex. 4 | Ex. 5 |
| --- | --- | --- | --- |
| NVP | 52.81 | 52.81 | 77.33 |
| HEMA | 6.02 | 6.02 | 0.44 |
| EGDMA | 0.50 | 0.50 | 0.11 |
| Propylene Glycol | 10.00 | 10.00 | 8.84 |
| Vazo 64 | 0.20 | 0.20 | 0.44 |
| MPEG-Silane16 | 8.52 | 8.52 | — |
| TRIS | 7.96 | 7.96 | — |
| SIGMA | 13.97 | 13.97 | — |
| DMA | — | — | 2.21 |
| TBE | — | — | 8.83 |
| CIX-4 | — | — | 0.88 |
| Poloxamer 407DM | — | — | 0.88 |
| Reactive Blue 247 | 0.20 | 0.02 | 0.02 |

The monomeric mixtures were cast into contact lenses by introducing the monomeric mixture to a polypropylene mold assembly. Then, the mold assembly and monomeric mixture were thermally cured for about 3.0 hours to form a contact lens. The resultant contact lenses were released from the mold assembly, extracted twice in 100% water for 10 minutes each and placed in a borated buffer solution (BBS) before being autoclaved.

Figure 3:
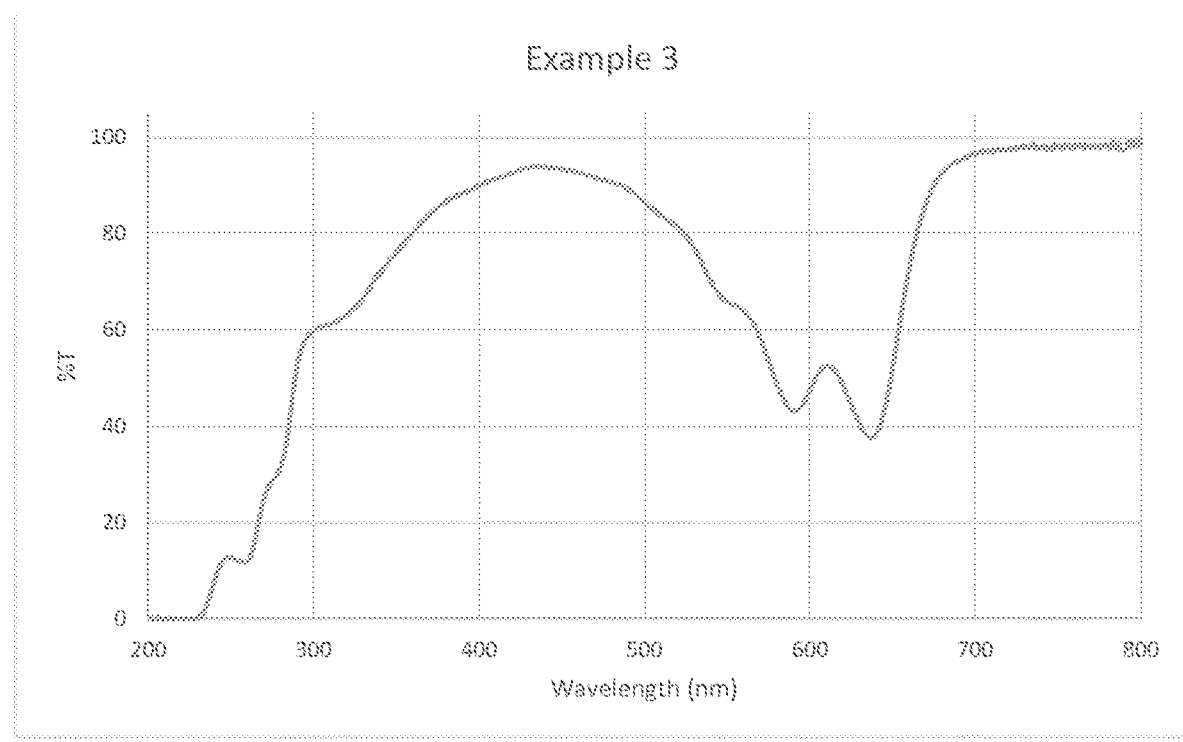
FIG. 3 is a graph illustrating the percent transmission of red-light through the lens of Example 3.
Figure 4:
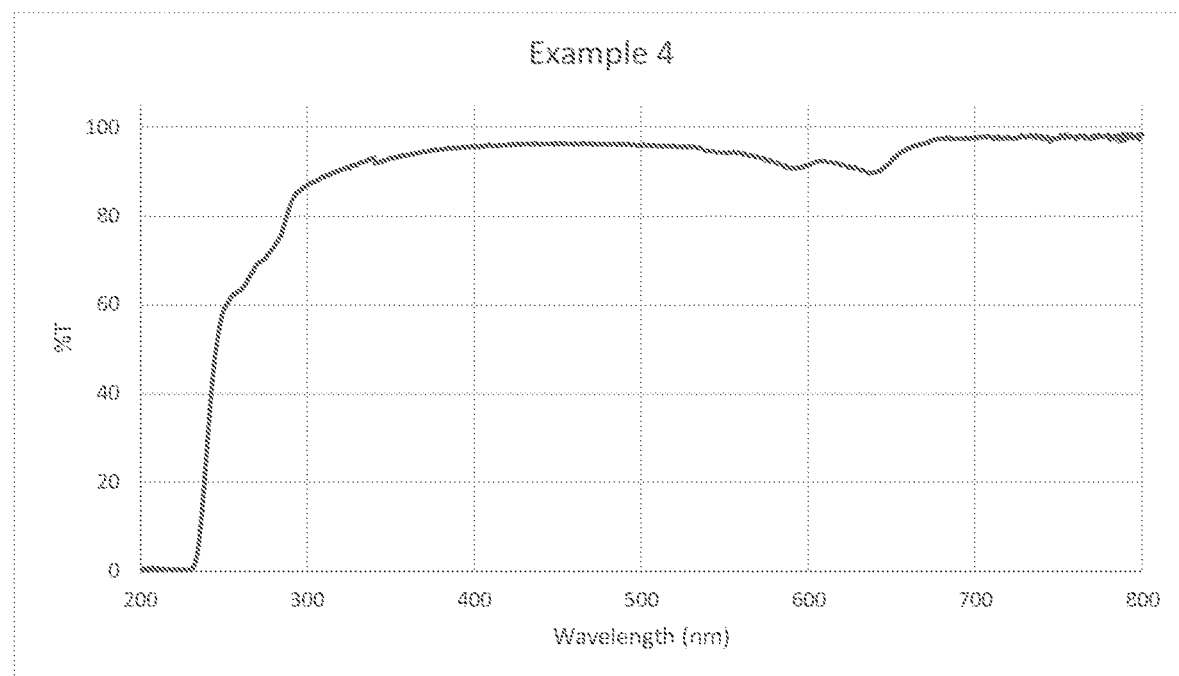
FIG. 4 is a graph illustrating the percent transmission of red-light through the lens of Example 4.
Figure 5:
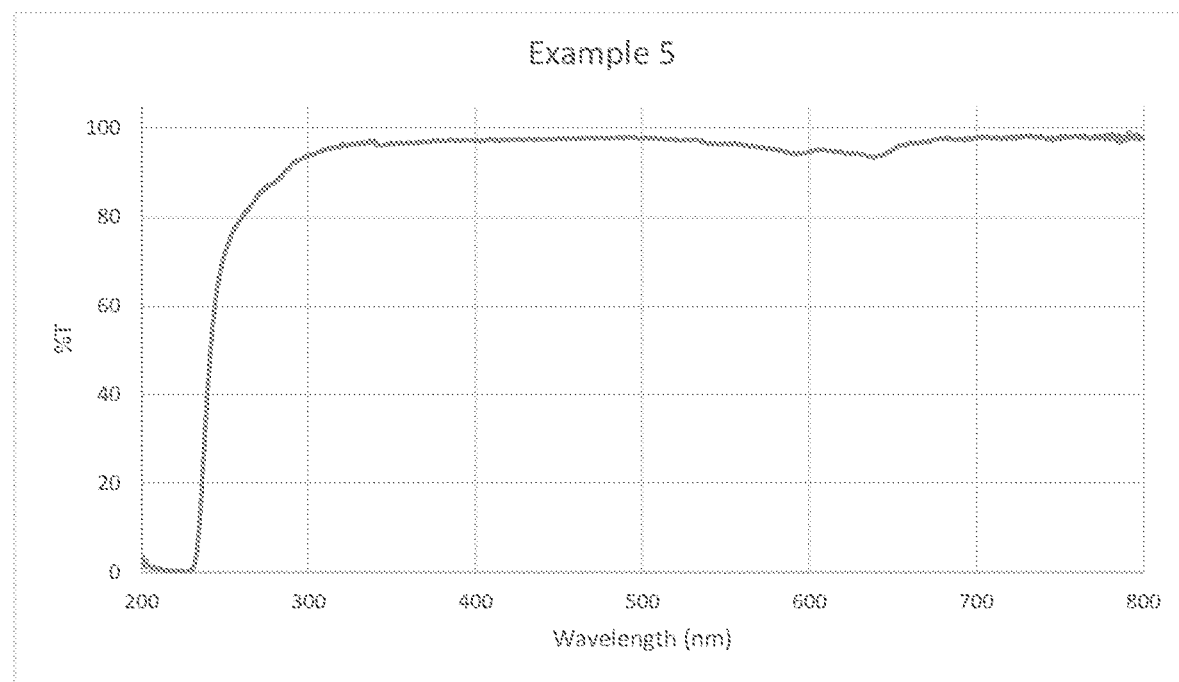
FIG. 5 is a graph illustrating the percent transmission of red-light through the lens of Example 5.

The lenses of Examples 3-5 were then individually placed onto a horizontal integrating sphere for contact lens measurement. The transmittance spectrum was obtained from 200 nm to 800 nm. FIGS. 3-5 are each a graph illustrating the percent transmission of red-light through the lens of Examples 3-5, respectively.

Various features disclosed herein are, for brevity, described in the context of a single embodiment, but may also be provided separately or in any suitable sub-combination. All combinations of the embodiments are specifically embraced by the illustrative embodiments disclosed herein just as if each and every combination was individually and explicitly disclosed. In addition, all sub-combinations listed in the embodiments describing such variables are also specifically embraced by the present compositions and are disclosed herein just as if each and every such sub-combination was individually and explicitly disclosed herein.

It will be understood that various modifications may be made to the embodiments disclosed herein. Therefore the above description should not be construed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the features and advantages appended hereto.

What is claimed is:
1. An ophthalmic device which is a polymerization product of a monomeric mixture comprising:
(a) greater than 50 wt. %, based on the total weight of the monomeric mixture, of one or more non-silicone-containing hydrophilic monomers;
(b) one or more crosslinking agents; and
(c) one or more red-light blocking compounds blocking greater than 5% to about 25% of red-light transmission through the ophthalmic device at a wavelength of from about 550 nanometers (nm) to about 800 nm, wherein the one or more red-light blocking compounds have one or more ethylenically unsaturated reactive end groups.

2. The ophthalmic device according to claim 1, wherein the one or more non-silicone-containing hydrophilic monomers are selected from the group consisting of an unsaturated carboxylic acid, an acrylamide, a vinyl lactam, a poly(alkyleneoxy)(meth)acrylate, (meth)acrylic acid, a hydroxyl-containing-(meth)acrylate, a hydrophilic vinyl carbonate, a hydrophilic vinyl carbamate monomer, a hydrophilic oxazolone monomer, and mixtures thereof.

3. The ophthalmic device according to claim 1, wherein the one or more non-silicone-containing hydrophilic monomers are selected from the group consisting of N,N-dimethylacrylamide, N,N-dimethylmethacrylamide, N-vinyl-2-pyrrolidone, N-vinyl caprolactam, N-vinyl-2-piperidone, 2-hydroxyethyl methacrylate, N-(2-hydroxyethyl)methacrylamide, glyceryl methacrylate, N-methacryloyl glycine, (2-hydroxy-3-methacryloylpropyl)-4-methoxy phenyl ether and mixtures thereof.

4. The ophthalmic device according to claim 1, wherein the one or more crosslinking agents are bi- or polyfunctional crosslinking agents comprising two or more reactive functional groups.

5. The ophthalmic device according to claim 1, wherein the one or more red-light blocking compounds comprise one or more red-light blocking compounds blocking greater than about 5% to about 25% of red-light transmission through the ophthalmic device at a wavelength of from about 550 nm to about 700 nm, wherein the one or more red-light blocking compounds have one or more ethylenically unsaturated reactive end groups.

6. The ophthalmic device according to claim 1, wherein the one or more red-light blocking compounds comprise one or more red-light blocking compounds blocking greater than about 5% to about 25% of red-light transmission through the ophthalmic device at a wavelength of from about 650 nm to about 680 nm, wherein the one or more red-light blocking compounds have one or more ethylenically unsaturated reactive end groups.

7. The ophthalmic device according to claim 1, wherein the one or more red-light blocking compounds comprise one or more red-light blocking compounds blocking from about 10% to about 15% of red-light transmission through the ophthalmic device at a wavelength of from about 550 nm to about 800 nm, wherein the one or more red-light blocking compounds have one or more ethylenically unsaturated reactive end groups.

8. The ophthalmic device according to claim 1, wherein the one or more red-light blocking compounds comprise one or more red-light blocking compounds blocking from about 10% to about 15% of red-light transmission through the ophthalmic device at a wavelength of from about 550 nm to about 700 nm, wherein the one or more red-light blocking compounds have one or more ethylenically unsaturated reactive end groups.

9. The ophthalmic device according to claim 1, wherein the one or more red-light blocking compounds comprise one or more red-light blocking compounds blocking greater from about 10% to about 15% of red-light transmission through the ophthalmic device at a wavelength of from about 650 nm to about 680 nm, wherein the one or more red-light blocking compounds have one or more ethylenically unsaturated reactive end groups.

10. The ophthalmic device according to claim 1, wherein the one or more ethylenically unsaturated reactive end groups of the one or more red-light blocking compounds comprise one or more (meth)acrylate end groups.

11. The ophthalmic device according to claim 1, wherein the one or more ethylenically unsaturated reactive end groups are represented by the following structure:

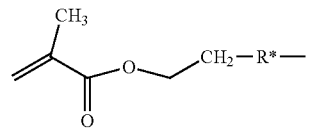

wherein R* is a linking group or bond.

12. The ophthalmic device according to claim 1, wherein the one or more red-light blocking compounds are represented by the following structure:

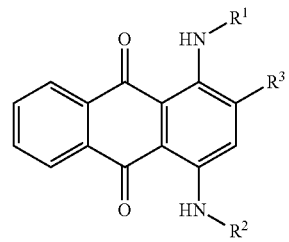

wherein $R^1$ and $R^2$ are hydrogen or a methacrylate-containing reactive end group, with at least one of $R^1$ and $R^2$ being a methacrylate-containing reactive end group; and $R^3$ is hydrogen or a sulfonate group.

13. The ophthalmic device according to claim 1, wherein the one or more red-light blocking compounds are represented by the following structure:

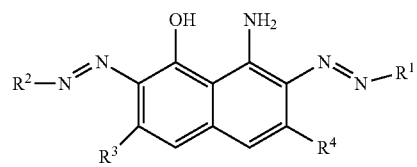

wherein $R^1$ and $R^2$ are hydrogen or an ethylenically unsaturated reactive end group, with at least one of $R^1$ and $R^2$ being an ethylenically unsaturated reactive end group; and $R^3$ and $R^4$ are independently hydrogen or a sulfonate group.

14. The ophthalmic device according to claim 1, wherein the monomeric mixture comprises:
(a) greater than 50 wt. % and up to 90 wt. %, based on the total weight of the monomeric mixture, of the one or more non-silicone-containing hydrophilic monomers;
(b) about 0.1 to about 2.0 wt. %, based on the total weight of the monomeric mixture, of the one or more crosslinking agents; and (c) about 0.02 to about 0.3 wt. %, based on the total weight of the monomeric mixture, of the one or more red-light blocking compounds.

15. The ophthalmic device according to claim 1, wherein the monomeric mixture further comprises one or more non-bulky organosilicon-containing monomers comprising a compound represented by the following structure:

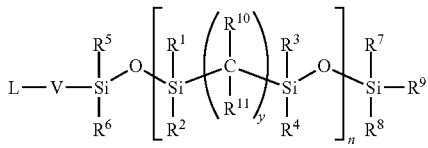

wherein L is ethylenically unsaturated polymerizable group, V is a linker group or a bond; $R^1$, $R^2$, $R^3$, $R^4$, $R^5$, $R^6$, $R^7$, $R^8$, and $R^9$ are independently hydrogen, an alkyl group, a haloalkyl group, a cycloalkyl group, a heterocycloalkyl group, an alkenyl group, a halo alkenyl group, or an aromatic group; $R^{10}$ and $R^{11}$ are independently hydrogen or alkyl group wherein at least one of $R^{10}$ and $R^{11}$ is hydrogen; y is 2 to 7 and n is 1 to 100, or a compound represented by the following structure:

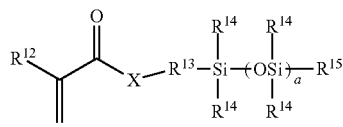

wherein $R^{12}$ is H or methyl; X is O or $NR^{16}$; wherein $R^{16}$ is hydrogen or $C_1$ to $C_4$ alkyl, which may be further substituted with one or more hydroxyl groups; $R^{13}$ is a divalent alkyl group, which may further be functionalized with a group selected from the group consisting of an ether group, a hydroxyl group, a carbamate group and combinations thereof; each $R^{14}$ is independently a phenyl or $C_1$ to $C_4$ alkyl which may be substituted with fluorine, hydroxyl or an ether; $R^{15}$ is a $C_1$ to $C_4$ alkyl; and a is 2 to 50.

16. The ophthalmic device according to claim 1, wherein the monomeric mixture further comprises one or more bulky siloxane monomers represented by the following structure:

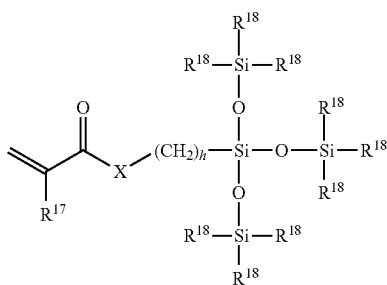

wherein X denotes —O— or —$NR^{19}$— where each $R^{19}$ is hydrogen or a $C_1$-$C_4$ alkyl; $R^{17}$ independently denotes hydrogen or methyl; each $R^{18}$ independently denotes a $C_1$-$C_6$ alkyl radical, a phenyl radical or a group represented by the following structure:

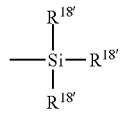

wherein each $R^{18'}$ independently denotes a $C_1$-$C_6$ alkyl radical or a phenyl radical; and h is 1 to 10; or the following structure:

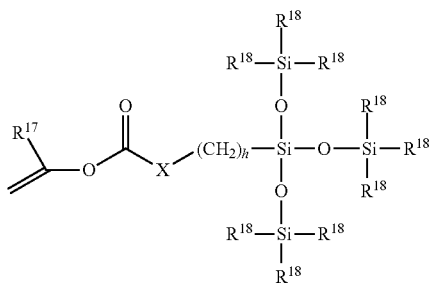

wherein X denotes —$NR^{19}$—; wherein $R^{19}$ denotes hydrogen or a $C_1$-$C_4$ alkyl; $R^{17}$ denotes hydrogen or methyl; each $R^{18}$ independently denotes a $C_1$-$C_6$ alkyl radical, a phenyl radical or a group represented by the following structure:

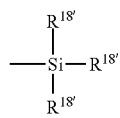

wherein each $R^{18'}$ independently denotes a $C_1$-$C_6$ alkyl radical or a phenyl radical; and h is 1 to 10.

17. The ophthalmic device according to claim 1, which is a contact lens or an intraocular lens.

18. A method of making an ophthalmic device, the method comprising:
    (a) providing a monomeric mixture comprising:
        (i) greater than 50 wt. %, based on the total weight of the monomeric mixture, of one or more non-silicone-containing hydrophilic monomers;
        (ii) one or more crosslinking agents; and
        (iii) one or more red-light blocking compounds blocking greater than about 5% to about 25% of red-light transmission through the ophthalmic device at a wavelength of from about 550 nanometers (nm) to about 800 nm, wherein the one or more red-light blocking compounds have one or more ethylenically unsaturated reactive end groups;
    (b) subjecting the monomeric mixture to polymerizing conditions to provide a polymerized ophthalmic device, and
    (c) hydrating the polymerized ophthalmic device.

19. The method according to claim 18, wherein the monomeric mixture comprises:
    (i) greater than 50 wt. % and up to 90 wt. %, based on the total weight of the monomeric mixture, of the one or more non-silicone-containing hydrophilic monomers;
    (ii) about 0.1 to about 2.0 wt. %, based on the total weight of the monomeric mixture, of the one or more crosslinking agents; and
    (iii) about 0.02 to about 0.3 wt. %, based on the total weight of the monomeric mixture, of the one or more red-light blocking compounds.

20. A method for slowing, inhibiting or preventing myopia progression in a subject in need thereof, the method comprising:
(a) providing an ophthalmic device which is a polymerization product of a monomeric mixture comprising:
  (i) greater than 50 wt. %, based on the total weight of the monomeric mixture, of one or more non-silicone-containing hydrophilic monomers;
  (ii) one or more crosslinking agents; and
  (iii) one or more red-light blocking compounds blocking greater than about 5% to about 25% of red-light transmission through the ophthalmic device at a wavelength of from about 550 nanometers (nm) to about 800 nm, wherein the one or more red-light blocking compounds have one or more ethylenically unsaturated reactive end groups; and
(b) inserting the ophthalmic device into an eye of the subject.

* * * * *